United States Patent [19]

Lundberg et al.

[11] Patent Number: 5,149,523
[45] Date of Patent: Sep. 22, 1992

[54] POLYSTYRENESULFONATE-DRUG COMPLEX AND SOLID DOSAGE FORMS THEREOF

[75] Inventors: Per J. Lundberg, Mölndal; Karin Wingstrand, Västra Frölunda; Kjell H. Andersson, Fjäras; Leif Simonsson, Göteborg, all of Sweden

[73] Assignee: Aktiebolaget Hassle, Mölndal, Sweden

[21] Appl. No.: 629,877

[22] Filed: Dec. 19, 1990

Related U.S. Application Data

[63] Continuation-in-part of Ser. No. 539,863, Jun. 18, 1990, Pat. No. 5,068,272.

[30] Foreign Application Priority Data

Jun. 29, 1989 [SE] Sweden .................................. 8902236
Dec. 7, 1990 [SE] Sweden .................................. 9003902

[51] Int. Cl.$^5$ ...................... A61K 31/74; A61K 9/14; A61K 31/745
[52] U.S. Cl. .................................. 424/78.1; 424/488; 424/78.08
[58] Field of Search ..................... 424/78.1, 488, 78.08

[56] References Cited

U.S. PATENT DOCUMENTS 4,221,778 1/1979 Raghunathan .................... 524/155

FOREIGN PATENT DOCUMENTS 0171528 2/1986 European Pat. Off. .
0254811 2/1988 European Pat. Off. .
1433920 4/1976 United Kingdom .
1457876 12/1976 United Kingdom .

OTHER PUBLICATIONS

Almgren, et al., Chem. Abstracts 112, Abstract 7180$_p$, 1990.
Amsel, et al, Unique Oral Controlled Release Systems: Design and Evaluation, pp. 83-93, Pergamon Press, New York, 1988.
Raghunathan, et al., J. Pharm. Sci. 70, 379-384, 1981.

Primary Examiner—Johann Richter
Attorney, Agent, or Firm—White & Case

[57] ABSTRACT

Almokalant (p-INN), 4-[3-]ethyl[3-(propylsulfinyl)-propyl]amino[-2-hydroxypropoxy]-benzonitrile, having the formula

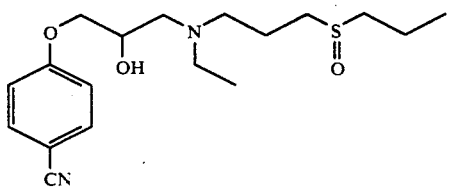

is a member of a group of compounds useful in the treatment of cardiac arrhythmias. Enhanced stability, palatability, and technical properties of almokalant can be achieved when it is complexed as a salt with polystyrenesulfonic acid. Accordingly, the invention encompasses the almokalant salt and processes for the preparation of said salt. The invention further encompasses solid oral pharmaceutical dosage forms containing the almokalant-polystyrenesulfonate complex as well as methods for their manufacture as medicaments with action against cadiac arrhythmias.

10 Claims, No Drawings

POLYSTYRENESULFONATE-DRUG COMPLEX AND SOLID DOSAGE FORMS THEREOF

This application is a Continuation-in-Part of copending patent application Ser. No. 07/539,863 filed Jun. 18, 1990, now U.S. Pat. No. 5,068,272.

FIELD OF THE INVENTION

The invention relates to a novel polystyrenesulfonate and to processes for its preparation. The invention also relates to solid dosage forms of the antiarrhythmic drug almokalant (p-INN) formulated as immediate release (IR) tablets and extended release (ER) tablets as well as processes for manufacture thereof.

More particularly, the present invention relates to the salt of almokalant (p-INN), 4-[3-[ethyl[3-(propylsulfinyl) propyl]amino]-2-hydroxypropoxy]benzonitrile, with polystyrenesulfonic acid, to its preparation, and to its manufacture in solid dosage forms as an agent for treatment of cardiac arrhythmias.

BACKGROUND OF THE INVENTION

Our prior patent application PCT/SE88/00691, filed on Dec. 20, 1988, relates to a group of novel compounds which are useful in the treatment, acute as well as long term, of cardiac arrhythmias of diverse etiology. Among the compounds included in the group of compounds disclosed in said application is almokalant (p-INN), 4-[3-[ ethyl[3-(propylsulfinyl)propyl]amino]-2-hydroxypropoxy]benzonitrile having the formula

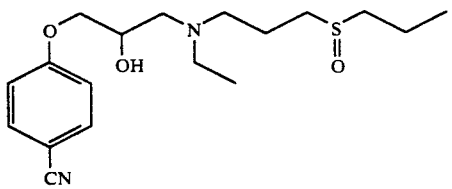

which can be obtained as a stereoisomeric mixture as well as in the form of the different stereoisomers, for instance:
4-[3-[ethyl[3-(propylsulfinyl)propyl]amino]-2(R)-hydroxypropoxy]benzonitrile,
4-[3-[ethyl[3-(propylsulfinyl)propyl]amino]-2(S)-hydroxypropoxy]benzonitrile.

The stereoisomeric mixture as well as the above mentioned pure stereoisomers can be obtained by oxidizing the appropriate 4-[3[ethyl[3-(propylthio)-propyl]amino]-2-hydroxy]benzonitrile with m-chloroperbenzoic acid or analogous to methods disclosed in the above mentioned prior patent application.

Almokalant in its free base form is an oil. It is a viscous, sticky substance, problematic to handle in the manufacture of solid dosage forms. It has a pronounced tendency to give a repellent odorous degradation product with a smell resembling old onions. No solid dosage forms containing the polystyrene sulphonate complex of almokalant have been reported. The polystyrenesulphonate complex of almokalant is described in the European patent application EP 90850242.0.

Several different ways were tested in order to prepare a solid dosage form of almokalant. Commonly used methods had the following disadvantages.

Due to the instability of the base and its tendency to worsen tablet binding properties, solid dosage forms of the free base are difficult to produce. See further reference example III.

Tablets prepared by conventional technique, with almokalant dissolved in an acidic granulating solution, have inferior stability properties and develop a repelling onion-like odor. See further reference examples I and III.

The use of complexes of drug substances with ion exchange resins in pharmaceutical formulation is described previously. A way to obtain a controlled release suspension containing codeine is described by Amsel L.P. et al. "Unique Oral Controlled Release Systems": In-Vivo Drug Release Pattern pp. 83-93 where a complex between codeine and an ion exchange resin is coated with a diffusion membrane and then formulated into a suspension. In addition, Pennwalt Corporation has published a series of patents describing the use of ion exchange resins having pharmacologically active substances absorbed thereon for use in controlled release preparations either as such or further coated with diffusion membranes (U.S. Pat. No. 4,221,778, EP 0171 528, EP 0 254 811). Other uses of ion exchange resin complexes with drugs in pharmaceutical formulation is for example summarized by Raghunathan et al. J Pharm Sci 1981, 70, (No. 4), 379-384.

DESCRIPTION OF THE INVENTION

It has now been found that the salt of almokalant with polystyrenesulfonic acid is a valuable new product having the same basic antiarrhythmic effect as almokalant but being a solid.

Accordingly the present invention relates to the salt of almokalant with polystyrenesulfonic acid.

According to one embodiment of the salt according to the invention, almokalant is present in the form of a stereoisomeric mixture.

According to another embodiment of the present invention almokalant is present in the form of one of the pure stereoisomers.

Examples of stereoisomers are, in addition to the two stereoisomers mentioned earlier, the following:
4-[3-[ethyl[3-((R*)-propylsulfinyl) propyl]amino]-2(R)-hydroxypropoxy]benzonitrile
4-[3-[ethyl[3-((S*)-propylsulfinyl) propyl]amino]-2(R)-hydroxypropoxy]benzonitrile 4-[3-[ethyl[3-((R*)-propylsulfinyl) propyl]amino]-2(S)-hydroxypropoxy]benzonitrile 4-[3-[ethyl[3-((S*)-propylsulfinyl)-propyl]amino]-2(S)-hydroxypropoxy]benzonitrile The present invention also relates to a process for the preparation of the salt according to the present invention, which process comprises reacting almokalant with polystyrenesulfonic acid.

Polystyrenesulfonic acid is preferably used in the form of small particles.

Usually the polystyrenesulfonic acid is crosslinked with divinylbenzene, the degree of crosslinking preferably being 2–10%.

According to one embodiment of the process according to the invention small particles of polystyrenesulfonic acid, either in the acid (H+) form or in the form of a salt with a metal ion suited for ion exchange reactions, e.g. Na+, K+ or Ca$^{2+}$, are added to a solution of almokalant and of a suitable salt of said compound, respectively, in a suitable reaction medium.

According to another embodiment of the process according to the invention small particles of polystyrene-sulfonic acid in the form of a salt with a metal ion suited for ion exchange reactions are packed into a column for ion exchange operations and a solution of almokalant in the form of a suitable salt is applied to the column.

The invention further relates to a method of preventing or reducing cardiac arrhythmias in mammals, including man, which comprises administering to a host in need of such treatment an effective amount of the salt of almokalant with polystyrenesulfonic acid.

The invention yet further relates to the salt of almokalant with polystyrenesulfonic acid for use as a medicament, particularly as an antiarrhythmic agent.

The invention also relates to the use of the salt of almokalant with polystyrenesulfonic acid for the manufacture of medicaments with action against cardiac arrhythmias.

The following non-limiting examples further illustrate the invention.

EXAMPLE 1

The polystyrenesulfonate of 4-[3-[ethyl[3-(propylsulfinyl)-propyl]amino]-2-hydroxypropoxy]benzonitrile To a stirred solution of 4-[3-[ethyl[3-(propylsulfinyl)-propyl]amino]-2-hydroxypropoxy]benzonitrile (92.28 g) in methanol (900 ml) was added polystyrenesulfonic acid (63.15 g) at 0° C. under nitrogen atmosphere. Stirring was continued for 18 h. The resin Was filtered, washed With methanol (500 ml), extracted in a Soxhlet extractor at room temperature overnight with ethanol and finally dried under high vacuum to constant weight. Analysis showed 59.3% binding of active substance.

EXAMPLE 2

The polystyrenesulfonate of 4-[3-[ethyl[3-(propylsulfinyl)-propyl]amino]-2-hydroxypropoxy]benzonitrile To a stirred solution of 4-[3-[ethyl[3-(propylsulfinyl)-propyl]amino]-2-hydroxypropoxy]benzonitrile·HCl (5.5 g) in ethanol:water (1:1) (30 ml) was added sodium polystyrenesulfonate (5 g) at room temperature. After 30 minutes the resin was filtered and washed with ethanol:water (1:1) three times, and dried under high vacuum to constant weight.

Analysis showed 32% binding of active substance.

EXAMPLE 3

4-[3-[ethyl[3-(propylsulfinyl)propyl]amino]-2-hydroxypropoxy]benzonitrile, 2.45 g of 4-[3-[ethyl[3-(propylthio)propyl]amino]-2-hydroxypropoxy]benzonitrile, and 1.4 g p-toluenesulfonic acid were mixed in 50 ml of ethanol. The mixture was cooled to −10° C. and 1.7 g of m-chloroperbenzoic acid was added in small portions. The mixture was stirred for 0.5 hour at −10° C. and one hour at room temperature and then evaporated. The residue was dissolved in dichloromethane and washed with three portions of sodium carbonate and twice with water and thereafter dried over sodium sulfate, filtered and evaporated. The residue, 2.3 g yellow oil, was purified by column chromatography. Yield: 1.4 g of the title compound.

NMR: $^{13}$C in CDCl$_3$; 11.21, 11.33, 13.11, 16.02, 20.30, 20.43, 47.41, 47.45, 49.69, 49.95, 52.18, 52.41, 54.29, 54.41, 56.06, 56.09, 66.08, 70.41, 70.49, 103.76, 115.09, 118.83, 113.62, 161.88 ppm

EXAMPLE 4

4-[3-[ethyl[3-(propylsulfinyl)propyl]amino]-2(R)-hydroxypropoxy]benzonitrile

Oxidation of 4-[3-[ethyl[3-(propylthio)propyl]amino]-2(R)-hydroxypropoxy]benzonitrile with m-chloroperbenzoic acid was carried out as described for the stereoisomeric mixture in example 3.

$[\alpha]^{20}_D$ −18.6° (C=1.0, CH$_3$OH).

NMR: $^{13}$C in CDCl$_3$; 11.35, 11.47, 13.30, 16.24, 20.47, 20.62, 47.59, 47.63, 49.83, 50.12, 52.30, 52.57, 54.53, 54.66, 56.28, 56.31, 66.13, 70.52, 70.60, 104.08, 115.24, 119.02, 133.85, 162.0 ppm.

EXAMPLE 5

4-[3-[ethyl[3-(propylsulfinyl)propyl]amino]-2(S)-hydroxypropoxy]benzonitrile

The title compound was prepared in analogy with the method described in example 4 and example 3. $[\alpha]^{20}_D$ +18.0° (C=1.0, CHOH).

NMR: $^{13}$C in CDCl$_3$; 11.31, 11.43, 13.26, 16.18, 20.41, 20.57, 47.53, 47.58, 49.8, 50.08, 52.26, 52.53, 54.48, 54.61, 56.22, 56.24, 66.09, 70.48, 70.57, 104.0, 115.20, 118.97, 133.79, 161.96 ppm.

Any of the isomers prepared according to Examples 4 and 5 may replace the stereoisomeric mixture used in Examples 1 and 2.

EXAMPLE 6

4-[3-[ethyl[3-((S*)-propylsulfinyl)propyl]amino]-2(R)-hydroxypropoxy]benzonitrile a) Ethyl (3-(S*)-propylsulfinyl)propylamine A hot solution of 27.2 g (0.1 mol) of (-)-1,3,2-dioxaphosphorinane-5,5-dimethyl-2-hydroxy-4-(2-methoxyphenyl)-2-oxide and 17.73 g (0.1 mol) of racemic ethyl (3-propylsulfinyl)-propylamine in 750 ml of acetone and 32.5 ml of methanol was allowed to cool to room temperature, yielding 23.9 g of crystalline material. The experiment was repeated on a 0.25 mol scale, this time yielding 53.0 g of crystals. The combined crops were recrystallized five times from acetone-methanol finally yielding 8.95 g of salt.

A solution of 15.6 g (0.0392 mol) of trioctylamine in dichloromethane was shaken with 19.6 ml of 2M hydrochloric acid. The phases were separated and the organic layer was washed with water. The organic phase, now containing trioctylammonium chloride, was stirred for 90 min. with a solution of 8.8 g (0.0196 mol) of the above mentioned resolved salt in water. The phases were separated, and the organic layer was washed with water. The combined aqueous phases were washed with dichloromethane, and then brought to pH 11.5 with 10M sodium hydroxide. Extraction four times with dichloromethane yielded 2.3 g of laevorotatory amine base, arbitrarily denoted S* $[\alpha]^{20}_D$ −8.0° (c=1, CH$_3$OH).

$^{13}$C NMR (as salt With (-)-1,3,2-dioxaphosphorinane-5,5-dimethyl-2-hydroxy-4-(2-methoxyphenyl)-2-oxide); in CDCl$_3$: 10.80, 12.95, 15.81, 17.55, 19.49, 19.58, 20.41, 36.59, 36.61, 42.37, 45.50, 48.73, 53.67, 54.71, 76.79, 76.83, 77.34, 109.63, 119.69, 126.42, 126.50, 128.33, 128.93, 155.83.

b) (R)-4-(oxiranylmethoxy)benzonitrile

A solution of 2.71 g of (2S)-1-(4-cyanophenoxy)-3-methanesulfonyloxypropan-2-ol in 40 ml of 1,2-dimethoxyethane was stirred with 1.0 g of powdered sodium hydroxide at room temperature for 22 h, 10 ml of saturated sodium chloride solution was added, and the mixture was extracted twice with ether. Washing with 5% sodium hydrogen carbonate, drying over magnesium sulfate, filtration and evaporation gave 1.76 g of crystalline material, m.p. 67.5° C., $[\alpha]^{20}_D - 14.7°$ (c=1, acetone).

NMR: $^{13}$C in CDCl$_3$; 44.40, 49.71, 69.02, 104.59, 115.34, 118.95, 133.98, 161.66 ppm.

c) 4 [3-[ethyl[3-((S*)-propylsulfinyl)propyl]amino]-2(R)-hydroxypropoxy]benzonitrile A mixture of 3 g of ethyl (3-(S*)-propylsulfinyl)propylamine and 3.18 g of (R)-4-(oxiranylmethoxy)benzonitrile was refluxed for 16 h in 25 ml of isopropyl alcohol. After evaporation of the solvent, the crude product was dissolved in 2M hydrochloric acid, washed with ether, the solution brought to pH 11.5 with 2M sodium hydroxide and extracted with dichloromethane. Evaporation of the organic phase gave 6.11 g of an oil, $^{13}$C NMR in CDCl$_3$: 11.23, 13.17, 16.08, 20.46, 47.41, 49.98, 52.41, 54.46, 56.11, 66.05, 70.50, 103.80, 115.13, 118.92, 133.69, 161.92 ppm.

EXAMPLE 7

4-[3-[ethyl[3-((R*)-propylsulfinyl)propyl]amino]-2(S)-hydroxypropoxy]benzonitrile a) Ethyl(3-(R*)-propylsulfinyl)propylamine Resolution of racemic ethyl (3-propylsulfinyl)propylamine with (+)-1,3,2-dioxaphosphorinane-5,5-dimethyl-2-hydroxy-4-(2-methoxyphenyl)-2-oxide in analogy with example 1a gave dextrorotatory amine base. This compound, arbitrarily denoted R*, has the following data: $[\alpha]^{20}_D + 7.6°$ (c=1, CH$_3$OH).

$^{13}$C NMR (as salt With (+)-1,3,2-dioxaphosphorinane-5,5-dimethyl-2 hydroxy-4-(2-methoxyphenyl)-2-oxide); in CDCl$_3$: 10.92, 13.07, 15.93, 17.66, 19.56, 19.70, 20.52, 36.72, 36.73, 42.48, 45.61, 48.85, 53.79, 54.82, 76.92, 76.96, 77.45, 77.49, 109.73, 119.81, 126.54, 126.62, 128.44, 129.06, 155.95 b) (S)-4-(oxiranylmethoxy)benzonitrile

From 2.7 g (2R)-1-(4-cyanophenoxy)-3-methanesulfonyloxypropan-2-ol in analogy with example 1b was obtained 1.75 g crystalline material; m.p. 68.0° C. $[\alpha]^{20}_D + 14.5°$ (c=1, acetone)

$^{13}$C NMR in CDCl$_3$: 44.21, 49.58, 68.90, 104.25, 115.20, 118.86, 133.80, 161.53.

(c) 4-[3-[ethyl[3-((R*)-propylsulfinyl)propyl]amino]-2(s)-hydroxypropoxy]benzonitrile A mixture of 2.3 g of ethyl[(R*)-3-propylsulfinyl]propylamine and 3.18 g of (S)-4-(oxiranylmethoxy)benzonitrile in 19 ml of isopropyl alcohol was refluxed 16 h and thereafter worked up in analogy with 1c yielding 4.1 g of an oil; $[\alpha]^{20}_D - 26.5°$ (c=1, acetone)

$^{13}$C NMR in CDCl$_3$: 11.16, 13.05, 15.96, 20.37, 47.38, 49.87, 52.37, 54.31, 56.05, 66.10, 70.47, 103.65, 115.06, 118.78, 133.55, 161.86.

EXAMPLE 8

4-[3-[ethyl[3-((R*)-propylsulfinyl)propyl]amino]-2(R)-hydroxypropoxy]benzonitrile A mixture of 2.3 g of ethyl[(R*)(-3-propylsulfinyl)propylamine and 2.5 g of (R)-4-(oxiranylmethoxy)benzonitrile was refluxed for 16 h in 19 ml of isopropyl alcohol in analogy with example 1c. Traditional workup procedures gave 4.27 g of an oil; $[\alpha]^{20}_D - 13.4°$ (c=1, CH$_3$OH)

$^{13}$C NMR in CDCl$_3$: 11.58, 13.36, 16.29, 20.57, 47.70, 49.96, 52.41, 54.64, 56.36, 66.24, 70.63, 104.18, 115.33, 119.07, 133.91, 162.09.

EXAMPLE 9

4-[3-[ethyl[3-((S*)-propylsulfinyl)propyl]amino]-2(S)-hydroxypropoxy]benzonitrile A mixture of 2.3 g of ethyl[3-((S*)-propylsulfinyl)propylamine and 2.5 g of (S)- 4-(oxiranylmethoxy)benzonitrile in 19 ml of isopropyl alcohol was refluxed for 24 h in analogy with example 1c. Traditional workup procedures gave 3.65 g of an oil; $[\alpha]^{20}_D + 11.1°$ (c=1, CH$_3$OH).

$^{13}$C NMR in CDCl$_3$: 11.56, 13.33, 16.25, 20.54, 47.71, 49.92, 52.42, 54.53, 56.31, 66.33, 70.64, 104.03, 115.33, 119.06, 133.86, 162.11.

A further aim of the present invention is to provide solid dosage forms of the antiarrhythmic drug almokalant, formulated as IR-tablets and ER-tablets with improved stability and minimal odor. ER-tablets can be formulated by a variety of formulation principles, such as hydrophilic gel-matrix tablets, matrix tablets, membrane diffusion controlled formulations, osmotic pressure controlled dosage forms, etc.

As the use of solid substances in tablet manufacture in general is advantageous and facilitates the production, different ways to prepare solid dosage forms were investigated.

As it had been noticed that almokalant in acidic solutions has a good stability, which makes it possible to autoclave it without noteworthy degradation, the addition of acid compounds was tested.

Although complex-binding to ion-exchange resins of viscous, unstable, pharmacologically active agents to form a stable solid complex suitable for pharmaceutical processing has not been previously described, this was tested with almokalant.

Thus, it was tested to use the polystyrene sulfonate complex of almokalant in the formulation of pharmaceutical dosage forms. It was then unexpectedly found that almokalant polystyrene sulfonate complex (A-PSS), had a much better stability, less repelling odor and was much easier to handle in tablet manufacture.

To form ER tablets it is necessary to mix the formed complex with e.g. a hydrophilic matrix. It is especially preferable to use hydroxypropyl methylcellulose as the gel-forming substance.

EXAMPLE 10

Immediate release tablets of almokalant were prepared by mixing A-PSS 90 parts, lactose 85 parts, microcrystalline cellulose 91 parts and polyvinyl pyrrolidone 27 parts and then granulating the mixture with purified water.

After drying, the granulate was milled and then mixed with sodium stearyl fumarate and compressed to tablets.

A reference preparation was produced by dissolving the free base in a 2M hydrochloric acid solution and using this solution to granulate the excipients.

|   |   | A-PSS tablet Ex 10 | Ref. Ex I |
|---|---|---|---|
| 1. | A-PSS corresp. to almokalant | 50.0 | — |
|   | Almokalant | — | 50.0 |
| 2. | Lactose pwd | 84.5 | — |
|   | Lactose anhydrous | — | 106.8 |

|  | A-PSS tablet Ex 10 | Ref. Ex I |
| --- | --- | --- |
| Avicel ® PH 101 | 91.3 | 114.0 |
| Povidone ® K-25 | 26.8 | — |
| Polyvinyl pyrrolidone, cross-linked | — | 7.1 |
| Aerosil ® | — | 3.6 |
| 3. Water, purified | 105 | — |
| Hydrochloric acid 2M (corresp. to HCl) | — | 71.2 (5.2) |
| 4. Sodium stearyl fumarate | 5.8 | — |
| Magnesium stearate | — | 2.9 |
| Talcum | — | 11.5 |
| Polyvinyl pyrrolidone, cross-linked | — | 5.7 |

The A-PSS tablet was prepared by first mixing ingredients 1 and 2. The mixture was granulated with 3. After drying and milling, 4 was admixed, whereupon compression to tablets was performed on a Korsch Pharmapress 100.

The reference tablet (Ref. ex. I) was prepared by making a granulating solution of the ingredients 1 and 3. The powders in 2 were mixed and then granulated with the prepared solution. After drying and milling, the lubricant, glidant and disintegrant in 4 were admixed and tablets compressed on the same machine.

|  | A-PSS tablet Ex 10 | Ref. Ex I |
| --- | --- | --- |
| Punches: | 9 mm | 10 mm |
| Tablet weight: | 298 mg | 307 mg |
| Hardness: | 7.5 kP | 6.7 kP |
| Disintegration: | 1-2 min. | 1-2 min. |
| Stability data of storage in glass bottles. Degradation measured as area sum of byproducts in a HPLC-system | | |
| 0 month | 0.81 | 2.11 |
| 1 month in 25° C. | 0.88 | 2.83 |
| 1 month in 50° C. | 1.82 | 3.41 |
| 3.5 months in 25° C. | 0.88 | 2.87 |

EXAMPLE 11

Immediate release tablets of almokalant were prepared by mixing A-PSS 90 parts, lactose 85 parts, microcrystalline cellulose 91 parts and polyvinyl pyrrolidone 27 parts and then granulating the mixture with purified water.

After drying, the granulate was milled and then mixed with the lubricant sodium stearyl fumarate whereupon compression to tablets was done.

A reference preparation (Ref. ex. II) was produced by dissolving the free base in an aqueous tartaric acid solution and using this solution to granulate the excipients.

|  |  | A-PSS tablet Ex 11 | Ref. tablet Ex II |
| --- | --- | --- | --- |
| 1. | A-PSS corresp. to almokalant | 50.0 | — |
|  | Almokalant | — | 50.0 |
| 2. | Lactose pwd | 84.5 | — |
|  | Lactose anhydrous | — | 110.7 |
|  | Avicel ® pH 101 | 91.3 | 114.3 |
|  | Polyvidone ® K-25 | 26.8 | — |
| 3. | Water, purified | 105 | 57.1 |
|  | Tartaric acid | — | 21.5 |
| 4. | Sodium stearyl fumarate | 5.8 | 6.0 |
|  | Talcum | — | 12.0 |
|  | Polyvinyl pyrrolidone, cross-linked | — | 12.0 |
|  | Punches: | 9 mm | 10 mm |
|  | Tablet weight: | 298 mg | 331 mg |
|  | Hardness: | 7.5 kP | 5.9 kP |
|  | Disintegration: | 1-2 min. | 8 min. |

The A-PSS tablets were prepared by first mixing ingredients 1 and 2. The mixture was granulated with 3. After drying and milling 4 was admixed, whereupon compression to tablets was performed on a Korsch Pharmapress 100.

The reference tablet (Ref. ex. II) was prepared by making a granulating solution of 1 and 3. The powders in 2 were mixed and granulated with the solution. After drying and milling, the lubricant, glidant and disintegrant in 4 were admixed and tablets were compressed on the same machine.

The odor intensities of the two formulations were compared immediately after manufacturing and after 1 month of storage in glass bottles.

| | Odor intensity | |
| --- | --- | --- |
| | A-PSS tablet Ex 11 | Ref. tablet Ex II |
| Freshly prepared | + (some smell, but not of onions.) | ++ (pronounced smell of onions.) |
| 1 month | + (some smell, but not of onions.) | +++ (strong smell of onions.) |

EXAMPLE 12

Immediate release tablets of almokalant can be prepared in suitable strengths.

In Ex. 10 and 11 a 50 mg preparation was described. Below are examples of 70 mg and 1.8 mg preparations shown.

|  |  | Ex 12a 70 mg | Ex 12b 1.8 mg |
| --- | --- | --- | --- |
| 1. | A-PSS | 127 | 3.3 |
|  | Avicel ® PH 101 | 148 | 29 |
|  | Polyvidone ® K-90 | 35 | — |
| 2. | Polyvidone ® K-90 | 10 | — |
|  | Polyvidone ® K-25 | — | 4.7 |
|  | Water, purified | 161 | 19 |
| 3. | Avicel ® PH 102 coarse grade | — | 107 |
|  | Polyvinyl pyrrolidone, cross-linked | — | 4.3 |
|  | Sodium stearyl fumarate | 1.6 | 1.4 |

The A-PSS tablets were prepared by first mixing the ingredients in 1. The mixture was granulated with a solution made of the ingredients in 2. After drying and milling the ingredients in 3 were admixed, whereupon compression to tablets was performed on a Korsch Pharmapress 100.

| Punches: | 10 mm | 5.5 × 10.5 mm |
| --- | --- | --- |
| Tablet weight: | 322 mg | 150 mg |
| Hardness: | 9-10 kP | 9-10 kP |
| Disintegration (without discs): | 0.6-1.0 min. | 0.2-0.4 min. |

EXAMPLE 13

Extended release tablets of almokalant were prepared by mixing A-PSS 95 parts, hydroxypropyl methylcellulose (HPMC) 50 cps 40 parts, HPMC 10000 cps 160 parts and hydroxypropyl cellulose (HPC) 50 parts and then granulating the mixture with 99.5% ethanol. After drying, the granulate was milled and then mixed with sodium stearyl fumarate whereupon compression to tablets was done.

A reference preparation (Ref. ex. III) was made by dissolving the free base in ethanol (99.5%) and using this solution to granulate the dry excipients, and otherwise following the same method of production.

| Ingredient | Example 13 mg/tablet | Ref. ex. III mg/tablet |
|---|---|---|
| 1. A-PSS corresp. to almokalant | 50.0 | — |
|    Almokalant | — | 50.0 |
| 2. HPMC 50 cps (Metolose ® 60SH50) | 40.0 | 40.0 |
| 3. HPMC 10000 cps (Methocel ® E10MCR) | 160.00 | 160.00 |
| 4. HPC LF (Klucel ® LF) | 50.0 | 50.0 |
| 5. Ethanol 99.5% | 261 | 235 |
| 6. Sodium stearyl fumarate (Pruv ®) | 3.3 | 3.3 |

Ingredients 1 to 4 were mixed. The mixture was granulated with ethanol. After drying and milling the granulate was mixed with 6.

Compression to tablets was performed on a Korsch Pharmapress 100 with 11 mm circular punches. The tablet machine was equipped with compression force registration.

| Tablet weight: | 348 mg | 303 mg |
|---|---|---|
| Tablet compression force: | 8.6 kN | 12.3 kN |
| Tablet hardness: | 5.5 kP | 3.7 kP |

Tablets made using the free base have inferior binding properties.

| | Odor intensity | |
|---|---|---|
| | A-PSS tablets (Ex. 13) | Reference tablet (Ref. ex. III) |
| Freshly prepared | + (some smell, but not of onions.) | +++ (strong smell of onions.) |

The release rate was determined from 6 individual tablets using USP dissolution apparatus 2 with the paddle rotating at 100 rpm and the tablet placed in a stationary basket above the paddle. 500 ml buffer solution pH 6.8 kept at 37° C. was used as dissolution medium.

| hours | A-PSS tablet (Ex. 13) cumulative % released average (min-max) | Ref. tablet (Ref. ex. III) cumulative % released average (min-max) |
|---|---|---|
| 2 | 15 (14-15) | 28 (28-29) |
| 4 | 24 (23-25) | 43 (42-43) |
| 6 | 34 (33-35) | 55 (54-56) |
| 10 | 51 (48-52) | 74 (72-75) |
| 24 | 91 (87-93) | 102 (100-105) |

EXAMPLE 14

Extended release tablets of almokalant can be prepared in suitable strengths and with different release rates.

In Ex. 13 a preparation with 50 mg strength is described. Below follow examples of 10 mg and 100 mg.

| | | mg/tablet | |
|---|---|---|---|
| Ingredient | | 10 mg Ex. 14a | 100 mg Ex. 14b |
| 1. | A-PSS corresp. to almokalant | 10.0 | 100.0 |
| 2. | Lactose pwd | 100.0 | 40.0 |
| | HPMC 50 cps (Metolose ® 60SH50) | 27.6 | 39.2 |
| | HPMC 10000 cps (Methocel ® E10MCR) | 110.4 | 146.4 |
| | HPC LF (Klucel ® LF) | 25.0 | — |
| 3. | Polyethylene glycol 20M (Carbowax ® 20M) | 30.0 | — |
| | Polyethylene glycol 6000 (Carbowax ® 6000) | — | 42.0 |
| 4. | Water, purified | 70.0 | 98.1 |
| 6. | Sodium stearyl fumarate (Pruv ®) | 1.6 | 2.3 |

1 and 2 were mixed. The mixture was granulated with a solution made of 3 and 4. After drying and milling the granulate was mixed with 5.

Compression to tablets was performed on a Korsch Pharmapress 100. The tablet machine was equipped with compression force registration.

| Punches, diameter: | 10 mm | 11 mm |
|---|---|---|
| Tablet weight: | 314 mg | 459 mg |
| Tablet compression force (kN): | 11.0 | 11.4 |
| Tablet hardness (kP): | 8.2 | 5.4 |

The release rate was determined from 6 individual tablets using USP dissolution apparatus 2 with the paddle rotating at 100 rpm and the tablet placed in a stationary basket above the paddle. 500 ml buffer solution pH 6.8 kept at 37° C. was used as dissolution medium

| hours | 10 mg ER tablet Ex. 14a cumulative % released average (min-max) | 100 mg ER tablet Ex. 14b cumulative % released average (min-max) |
|---|---|---|
| 2 | 27 (27-28) | 17 (17-18) |
| 4 | 44 (43-45) | 28 (26-29) |
| 6 | — | 37 (35-39) |
| 8 | 72 (70-75) | — |
| 10 | — | 55 (52-56) |
| 12 | 105 (96-109) | — |
| 20 | — | 91 (84-95) |
| 24 | — | 100 (99-101) |

DISCUSSION

From the examples it is quite obvious that the use of almokalant free base in pharmaceutical formulation—apart for the inconvenience of handling a sticky viscous substance—results in dosage forms with inferior stability and palatability as well as in inferior technical properties. The use of almokalant-polystyrenesulfonate complex in pharmaceutical formulation eases the handling and results in more stable and more palatable dosage forms.

The best mode of carrying out the invention known at present is to prepare the formulation according o Example 14.

We claim:

1. A pharmaceutical composition comprising the salt of almokalant, 4-[3-[ethyl[3-(propyl-sulfinyl)propyl]amino]-2-hydroxypropoxy]benzonitrile, with polystyrenesulfonic acid and hydroxypropylmethylcellulose.

2. The pharmaceutical composition of claim 1 wherein the almokalant is in the form of a stereoisomer mixture or in the form of a pure stereoisomer thereof.

3. The pharmaceutical composition of claim 1 or 16 wherein the hydroxypropylmethylcellulose is low molecular weight hydroxypropylmethylcellulose.

4. The pharmaceutical composition of claim 1 or 16 wherein the hydroxypropylmethylcellulose is high molecular weight hydroxypropylmethylcellulose.

5. The pharmaceutical composition of claim 1 or 16 wherein the hydroxypropylmethylcellulose comprises both high and low molecular weight hydroxypropylmethylcellulose.

6. A dosage form according to claim 8 wherein the hydroxypropylmethylcellulose is low molecular weight hydroxypropylmethylcellulose.

7. A pharmaceutical dosage form of the salt almokalant 4-[3-[ethyl[3-(propylsulfinyl)propyl]amino]-2-hydroxypropoxy]benzonitrile, wherein said almokalant in the form of a complex with polystyrene sulphonate optionally mixed with pharmaceutical excipients forms an oral solid dosage form.

8. A dosage form according to claim 6 wherein the pharmaceutical excipients contain a hydrophilic matrix.

9. A dosage form according to claim 7 wherein the hydrophilic matrix is hydroxypropyl methylcellulose.

10. A dosage form of claim 8 wherein the hydroxypropylmethylcellulose is high molecular weight hydroxypropylmethylcellulose.

* * * * *